United States Patent [19]

Starzycki et al.

[11] 4,098,579
[45] Jul. 4, 1978

[54] INSTALLATION FOR CONDUCTING A SYNTHESIS REACTION OF UREA

[75] Inventors: Janusz Starzycki; Jadwiga Starzycka; Janusz Sobczak; Stanislaw Golembiowski, all of Pulawy; Ernest Pieczora; Stanislaw Kolanek, both of Kedzierzyn; Jerzy Simonides, Opole; Jozef Jendrzej, Kedzierzyn, all of Poland

[73] Assignee: Instytut Nawozow Sztucznych Zjednoczenie "Petrochemia", Pulawy, Poland

[21] Appl. No.: 774,068

[22] Filed: Mar. 3, 1977

[51] Int. Cl.² .............................. B01J 1/00; B01J 3/00; C07C 126/02
[52] U.S. Cl. ......................................... 23/283; 23/285; 23/290; 260/555 A; 261/114 VT
[58] Field of Search ........ 23/283, 289, 290, 285 (U.S. only); 260/555 A (U.S. only); 261/114 VT

[56] References Cited

U.S. PATENT DOCUMENTS

| 3,024,280 | 3/1962 | Braun .............................. 260/555 A |
| 3,293,149 | 12/1966 | Lengemann et al. ............. 23/283 X |
| 3,475,134 | 10/1969 | Weber et al. ...................... 23/283 X |
| 3,749,380 | 7/1973 | Strom et al. ...................... 23/283 X |

FOREIGN PATENT DOCUMENTS

| 344,716 | 4/1960 | Switzerland ..................... 260/555 A |

*Primary Examiner*—Morris O. Wolk
*Assistant Examiner*—Roger F. Phillips
*Attorney, Agent, or Firm*—Eric P. Schellin; Anne M. Kornbau

[57] ABSTRACT

Apparatus for synthesis of urea comprising a reaction vessel divided into a number of adjacent reaction zones by means of overflow-preventing plates with moving elements that are non-return valves.

6 Claims, 1 Drawing Figure

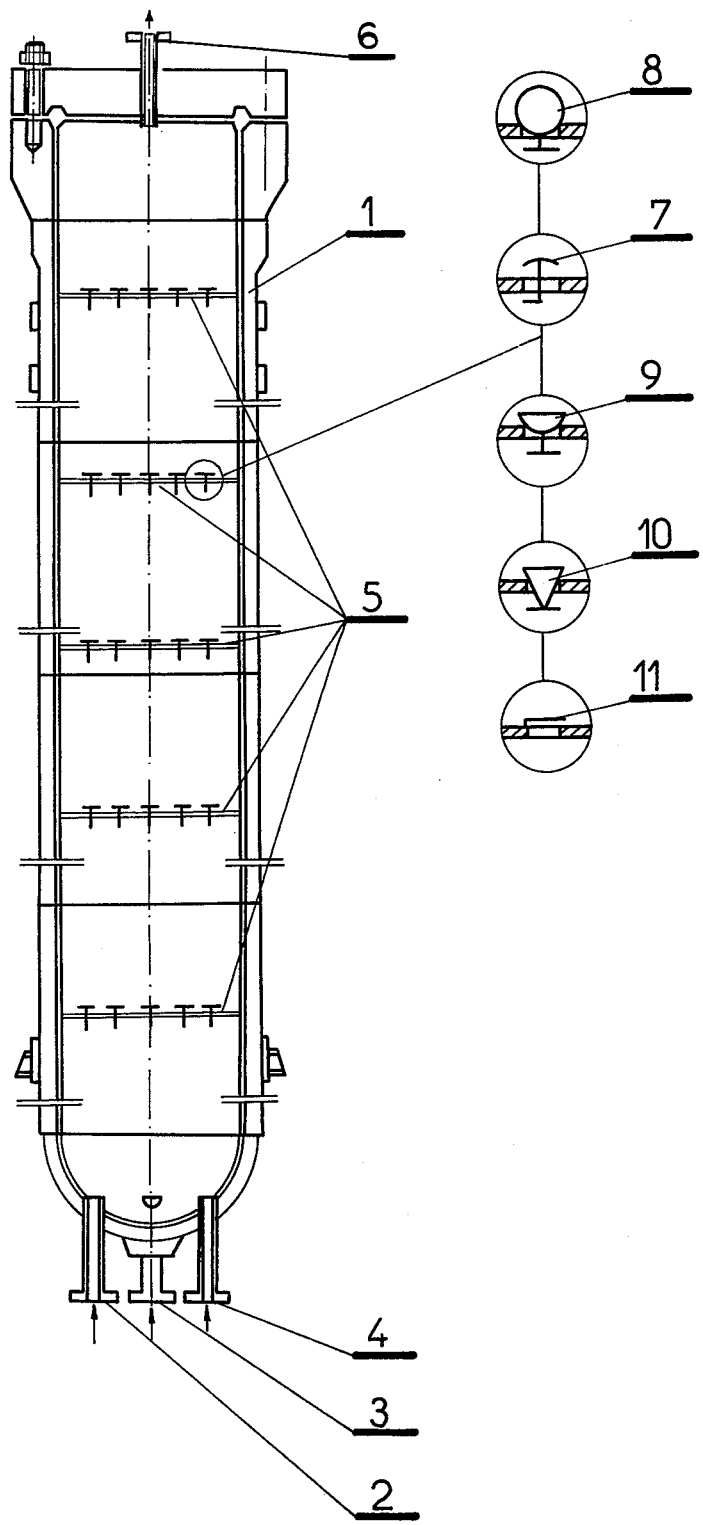

INSTALLATION FOR CONDUCTING A SYNTHESIS REACTION OF UREA

BACKGROUND OF THE INVENTION

The present invention relates to an apparatus for synthesizing urea from ammonia and carbon dioxide at a temperature of 100°–250° C, and under a pressure of 100–300 kg./cm. in the presence of unreacted feed, the feed being separated from an after-synthesis alloy and recycled to a synthesis reactor.

Synthesis of urea takes place at elevated temperature and pressure according to the following reactions:

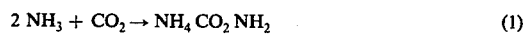

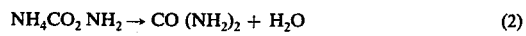

Reaction (1) is highly exothermic and proceeds rapidly, whereas reaction (2) is weakly endotheremic and requires a long time to attain a state of equilibrium. Consequently, reactors for the synthesis of urea have large capacities which influence considerably the costs of these reactors.

In the past, vertical cylindrical reactors for urea synthesis are constructed to have a small linear flow rate of about 1 cm./s. This results in strong circulations in the inside of the reactor because of high rate of flow of inlet streams, thermal effects of chemical reactions, and considerable differences in densities of the reaction mixture in the bottom part and the top part of the reactor. Consequently, the nature of flow is far from a piston flow, which kind of flow is advantageous for reaction (2).

It is known to use baffles of perforated plates in reactors in order to eliminate undesired circulations, cf. S. Yoshemura, *Hydrocarbon Processing*, 49, 6, pp. 111–115 (1970), and G. I. Nieupokajewa et al, *Chim. Prom.* No. 6, pp. 37–41 (1976). These baffles reduce to a certain degree linear rates in the reactor, but, due to the possibility of a bidirected flow, they do not eliminate internal circulations.

SUMMARY OF THE INVENTION

The present invention consists of a reactor containing within overflow-preventing baffle plates with round, oval, fissure-shaped, or other shaped orifices wherein elements are mounted within the orifices to provide an undirectional flow of the reaction mixture. For example, small valves, balls, hemispheres, cones, flaps, movable diaphragms, etc., may be used as such elements. The above-mentioned elements are fastened to the plates in the known manner as are overflow plates in rectifying columns. In the apparatus according to the present invention, the plates are mounted movably or immovably on the internal surfaces of the reactor. Where an anticorrosive insert is used in the reactor, the plates are mounted on the internal surfaces of this insert.

DESCRIPTION OF THE DRAWINGS

The drawing shows a reactor for urea synthesis according to the present invention.

Referring now to the drawing, there is shown a reactor 1, supplied from underneath with two streams: one of $NH_3$ by means of a connector pipe 2, another one of $CO_2$ by means of a connector pipe 3, and with a circulating aqueous solution of unreacted feed by means of a connector pipe 4. A stream of reaction mixture flows upward and is simultaneously branched, slowed down, and mixed on overflow-preventing plates 5 which have small valves 7 fastened thereto. The valves may be arranged in any manner on the plate, although the valves are preferably arranged in a regular pattern.

In the FIGURE, five overflow-preventing baffle plates 5 are shown by way of example. The plates are equipped with movable elements in the form of a ball 8, mushroom 7, hemisphere 9, cone 10, or plate 11. These elements give an unidirectional flow to the reaction mixture.

An after-reaction mixture is removed through a connector pipe 6.

Because the streams which enter the reactor are branched by the plates, the surfaces of contact of the reactants are increased at the bottom part of the reactor, speeding the rate of reaction of the carbonate synthesis slowing down the stream of reactants and eliminating backward circulations results in a piston-type flow of reactants, thus more closely achieving an equilibrium state. A greater amount of reacting $CO_2$ is provided to the urea obtained therefrom, yielding considerable gains of energy for decomposing unreacted feed. This results in an increase in load and a higher production of urea from 1m³ of reactor capacity.

The apparatus according to the invention is cheap and easy to assemble. When corrosion occurs, the installation can be temporarily replaced without long stand-stills of the reactor.

What we claim is:

1. In an apparatus for the synthesis of urea comprising (a) a vertically disposed reaction vessel having at least two fluid inlets thereto near the base thereof and at least one fluid outlet therefrom near the top thereof, and (b) a plurality of vertically spaced, horizontally disposed overflow-preventing baffle plates having a plurality of orifices therein and being mounted within said vessel, each of said baffle plates extending across the entire interior horizontal cross section of said vessel, (c) the improvement comprising non-return valves mounted in each of said orifices whereby reaction fluid flows upward through said vessel and through said orifices and valves, said valves preventing the downward backflow of reaction fluid and thus providing for unidirectional upward flow through the reaction vessel.

2. The apparatus of claim 1 wherein the non-return valves are spherical.

3. The apparatus of claim 1 wherein the non-return valves are mushroom-shaped.

4. The apparatus of claim 1 wherein the non-return valves are hemispherical.

5. The apparatus of claim 1 wherein the non-return valves are cone-shaped.

6. The apparatus of claim 1 wherein the non-return valves are plate-shaped.

* * * * *